United States Patent
Stewart et al.

(10) Patent No.: US 6,730,200 B1
(45) Date of Patent: May 4, 2004

(54) ELECTROCHEMICAL SENSOR FOR ANALYSIS OF LIQUID SAMPLES

(75) Inventors: Alan A. Stewart, Reading (GB); Steven Scott, Andover, MA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/926,726

(22) PCT Filed: Apr. 28, 2000

(86) PCT No.: PCT/GB00/01655

§ 371 (c)(1),
(2), (4) Date: Dec. 10, 2001

(87) PCT Pub. No.: WO00/79258

PCT Pub. Date: Dec. 28, 2000

(30) Foreign Application Priority Data

Jun. 18, 1999 (GB) .............................................. 9914238

(51) Int. Cl.[7] ............................................ G01N 27/327
(52) U.S. Cl. .............................. 204/403.11; 204/403.06; 204/403.1; 204/403.14; 427/2.13
(58) Field of Search .................... 204/403.06, 403.1, 204/403.11, 403.14; 427/2.13

(56) References Cited

U.S. PATENT DOCUMENTS

| | | | |
|---|---|---|---|
| 5,312,590 A | 5/1994 | Gunasingham | 204/403.1 |
| 5,509,410 A | 4/1996 | Hill et al. | 600/393 |
| 5,628,890 A | 5/1997 | Carter et al. | 204/403.05 |

FOREIGN PATENT DOCUMENTS

| | | | | |
|---|---|---|---|---|
| GB | 2 337 122 A | 11/1999 | | G01N/27/403 |
| WO | WO 91/09139 | 6/1991 | | C12Q/1/54 |
| WO | WO 99/13099 | 3/1999 | | C12Q/1/00 |
| WO | WO 99/13101 | 3/1999 | | C12Q/1/00 |

Primary Examiner—Alex Noguerda
(74) Attorney, Agent, or Firm—David L. Weinstein (57) ABSTRACT

An electrochemical cell having an auxiliary area that contains a redox species on a working electrode. The auxiliary area provides a low resistance current path between the working electrode and a pseudo reference/counter electrode. The auxiliary area is an integral part of the working electrode and allows an enhanced current to flow. The enhanced current adds to the measurement signal. This reduces non-monotonic current decay, which can lead to erroneous analyte measurements.

26 Claims, 5 Drawing Sheets

ELECTROCHEMICAL SENSOR FOR ANALYSIS OF LIQUID SAMPLES

This application is the national stage under 35 U.S.C. 371 of PCT/GB00/01655, filed Apr. 28, 2000.

BACKGROUND OF THE INVENTION

1. Field of the Invention

The invention relates to sensors for performing electrochemical analysis to determine concentrations of analytes in mixtures of liquids.

2. Discussion of the Art

Electrochemical assays for determining the concentrations of enzymes or their substrates in complex mixtures of liquids have been developed. In particular, biosensor strips for biomedical applications (e.g., whole blood analyses) have been developed for the detection of glucose levels in biological samples. In general, the biosensor strips comprise typical electrochemical cells in which there can be working electrodes, counter electrodes, and pseudo reference/counter electrodes. The potential of the working electrode is typically kept at a constant value relative to that of the pseudo reference/counter electrode.

Biosensor strips are used in the chemical industry, for example, to analyze complex mixtures. They are also used in the food industry and in the biochemical engineering industry. Biosensor strips are also useful in medical research or in external testing. In medical research, they can function as invasive probes (i.e., where they come into contact with a body fluid, such as whole blood or subcutaneous fluid). In external testing, they can function in a non-invasive manner (i.e., where they come into contact with blood withdrawn by a syringe or a pricking device).

A typical three-electrode sensor for blood analysis suitable for measuring the amount of analyte in a sample of liquid comprises (1) an active or working electrode that is coated with a layer containing an enzyme and a redox mediator, (2) a passive or dummy electrode that is coated with a layer containing a redox mediator but lacking an enzyme, and (3) a pseudo reference/counter electrode or counter electrode. When a sample of liquid containing a species for which the enzyme is catalytically active contacts the electrodes, the redox mediator transfers electrons in the catalyzed reaction. When a voltage is applied across the electrodes, a response current results from the reduction or oxidation of the redox mediator at the electrodes. The response current at the dummy electrode represents a background response of the electrode in contact with the sample. The response current at the working electrode is related to the concentration of the substrate. A corrected response current is calculated by subtracting the response current at the dummy electrode from the response current at the working electrode. This subtraction calculation substantially eliminates background interferences, thereby improving the signal-to-noise ratio in the sensor.

Non-monotonic current decay can occur in a system when the resistance between the working electrode and the pseudo reference/counter electrode is large. This type of current decay can complicate measurements of concentration of analyte.

SUMMARY OF THE INVENTION

In general, this invention provides an electrochemical cell having a working electrode having an auxiliary area that contains a redox species. The auxiliary area provides a current path of low resistance between the working electrode and a pseudo reference/counter electrode. The auxiliary area is an integral part of the working electrode. The auxiliary area allows an enhanced current to flow. The enhanced current helps to reduce or even substantially eliminate non-monotonic decay of the current transient. The auxiliary area of the working electrode is generally located closer to the pseudo reference/counter electrode than is the working area of the working electrode.

The auxiliary area of the working electrode does not contribute to an electrochemical measurement of the analyte of interest, because there is no catalytic component (e.g., enzyme) in the auxiliary area. As a result, the current associated with the auxiliary area is generated from simple oxidation, or reduction, of the redox species and follows a Cottrellian response. In the electrode configuration of this invention, the additive effect of the current is significant only during the first few seconds of the response, correcting any non-monotonic behavior of the current decay.

The enhanced current has no net effect during the period of time during which the measurement is being made, because the duration of the period is short. In a system containing two electrodes (e.g., a working electrode and a dummy electrode), an auxiliary area can be applied to the dummy electrode. The auxiliary area of the dummy electrode must be of the same size and shape as that of the auxiliary area of the working electrode. The auxiliary area of the dummy electrode and the auxiliary area of the working electrode are preferably positioned symmetrically with respect to the pseudo reference/counter electrode. This configuration produces an identical response at both auxiliary areas. Therefore, any effect on the measurement current is canceled out upon subtraction of the current of one electrode from the current of the other electrode.

In one aspect, the invention provides an electrochemical cell comprising a first electrode, which is referred to as a working electrode. The first electrode comprises a first working area and a first auxiliary area. The first working area comprises a working ink. The first auxiliary area comprises a first dummy ink. The working ink comprises an enzyme and a first redox mediator. The first dummy ink comprises a redox species, but lacks an enzyme. The redox species of the first dummy ink can be the same material as the redox mediator in the working ink.

The electrochemical cell can include a second electrode, which is referred to as a dummy electrode. The second electrode comprises a second working area and a second auxiliary area. The second working area comprises a second dummy ink, which comprises the first redox mediator, but lacks an enzyme. The second auxiliary area comprises the first dummy ink.

The electrochemical cell can include a pseudo reference/counter electrode. The first auxiliary area is preferably located closer to the pseudo reference/counter electrode than is the first working area. The second auxiliary area is preferably located closer to the pseudo reference/counter electrode than is the second working area.

The first working area can be larger in area than the first auxiliary area. The second working area can be larger in area than the second auxiliary area. The first working area can be smaller in area than the second working area and second auxiliary area in combination.

In another aspect, the invention provides a biosensor strip. The strip comprises an electrode support, a first electrode, i.e., a working electrode, a second electrode, i.e., a dummy electrode, and a pseudo reference/counter electrode. Each of the electrodes is disposed on and supported by the electrode support. The pseudo reference/counter electrode is spaced apart from the first electrode and second electrode. The biosensor strip can include a covering layer, which defines an enclosed is space over the electrodes. The covering layer has an aperture for receiving a sample for introduction into the enclosed space. The biosensor strip can also include at least one layer of mesh interposed in the enclosed space between the covering layer and the electrodes.

In another aspect, the invention provides a method of manufacturing an electrochemical cell. The method includes the steps of applying a working ink to a first electrode to form a first working area, and applying a first dummy ink to the first electrode to form a first auxiliary area. The first electrode is a working electrode. The method can also include the steps of applying a second dummy ink to a second electrode to form a second working area, and applying the first dummy ink to the second electrode to form a second auxiliary area. The second electrode is a dummy electrode.

Under some conditions, the current decay at the working electrode departs from the expected model. In particular, it is expected that the current will decrease monotonically over time and exhibit the behavior predicted by the Cottrell equation. However, when the dummy electrode imposes a significant current load on the pseudo reference/counter electrode, the current at the working electrode departs from classical behavior and may actually increase over some short time period. Glucose meters with which the biosensor strips of this invention are used have electronic features designed to detect invalid test results. One of these electronic features involves monitoring the current decay at the working electrode. If this decay is not monotonic, the meter will report an error condition and abort the test.

The auxiliary areas can reduce or substantially eliminate non-monotonic current decay during the first few seconds of a chronoamperometric test. Accordingly, it is possible to reduce or even eliminate the occurrence of errors on electrochemical sensors used to analyze blood glucose. The auxiliary areas on the dummy electrode and on the working electrode can help overcome errors by increasing the initial current spike of the working electrode and the dummy electrode. The current increase results from oxidation or reduction of the additional redox species introduced by the dummy ink. The current generated from the oxidation or reduction of the redox species has a low resistance path to the pseudo reference/counter electrode, which allows efficient oxidation or reduction of the redox species without substantial voltage drops.

Each of the first redox mediator and the redox species can be a ferrocene. Preferably, the enzyme is glucose oxidase.

Other features and advantages of the invention will be apparent from the descriptions of the embodiments thereof.

DETAILED DESCRIPTION

As used herein, the expression "working electrode" means an electrode where the reaction of interest takes place. The current is proportional to the concentration of the analyte, e.g., glucose, at the working electrode. The expression "dummy electrode" refers to an electrode that is similar to the working electrode, but lacks the substance that reacts with the analyte. The working electrode response is the sum of the responses of the analyte, e.g., glucose, and the background; the dummy electrode response is the response of the background. The expression "working ink" means a conductive ink printed on the working electrode. The working ink contains both a redox mediator and a substance for reacting with the analyte, e.g., glucose oxidase in the case of glucose. Depending upon the nature of the analyte, the substance for reacting with the analyte can be an enzyme or a substrate for an enzyme. The expression "dummy ink" means a conductive ink containing a redox species, but lacking a substance for reacting with the analyte. The expression "redox species" means any chemical compound that can be oxidized or reduced. The expression "redox mediator" means any redox species that can oxidize or reduce another molecule, typically an enzyme. Redox mediators relay the information from an oxidation/reduction reaction from an enzyme to an electrode. The expression "pseudo reference/counter electrode" means an electrode that functions as both a reference and a counter electrode. In conventional three electrode electrochemical systems, there are three electrodes: (1) a working electrode, (2) a reference electrode and (3) a counter electrode. The reaction that takes place at the working electrode is the reaction that is required to be monitored and controlled. The functions of the reference and counter electrodes are to ensure that the working electrode actually experiences the desired conditions, i.e. the correct potential. The function of the reference electrode is to measure the potential at the working electrode/sample interface as accurately as possible. In an ideal situation, no current passes through the reference electrode. The function of the counter electrode is to apply the correct potential difference between itself and the working electrode, such that the potential at the working electrode is the desired potential. The potential difference between the working electrode and the reference electrode is assumed to be the same as the desired potential at working electrode. If the measured potential is not the potential desired at the working electrode, the potential that is applied between the counter electrode and working is electrode is altered accordingly, i.e., the potential is either increased or decreased. The reaction at the counter electrode is also equal and opposite to the charge transfer reaction occurring at the working electrode, i.e., if an oxidation is occurring at the working electrode then a reduction will take place at the counter electrode, thereby allowing the sample to remain electrically neutral. In a two electrode system, there are two electrodes: (1) a working electrode (or in the case of biosensor strips described herein, two working electrodes, i.e. the so-called working electrode and the dummy electrode) and (2) a pseudo reference/counter electrode. The reason that the second electrode is called a pseudo reference/counter electrode is because the electrode does not act as an ideal reference electrode, but it still acts as a real counter electrode. In an ideal reference electrode, no current passes through it and it maintains a steady potential; in the case of a pseudo reference/counter electrode, current does pass through the pseudo reference/counter electrode, and thus, the pseudo reference/counter electrode does not maintain a steady potential. At low currents, the potential shift is small enough such that the response at the working electrode is not significantly affected, and hence the pseudo reference/counter electrode is designated a pseudo reference electrode. The pseudo reference/counter electrode still carries out its counter electrode function; however, in this case, the potential that is applied between the pseudo reference/counter electrode and the working electrode cannot be altered to compensate for changes in potential at the working electrode.

Figure 1:
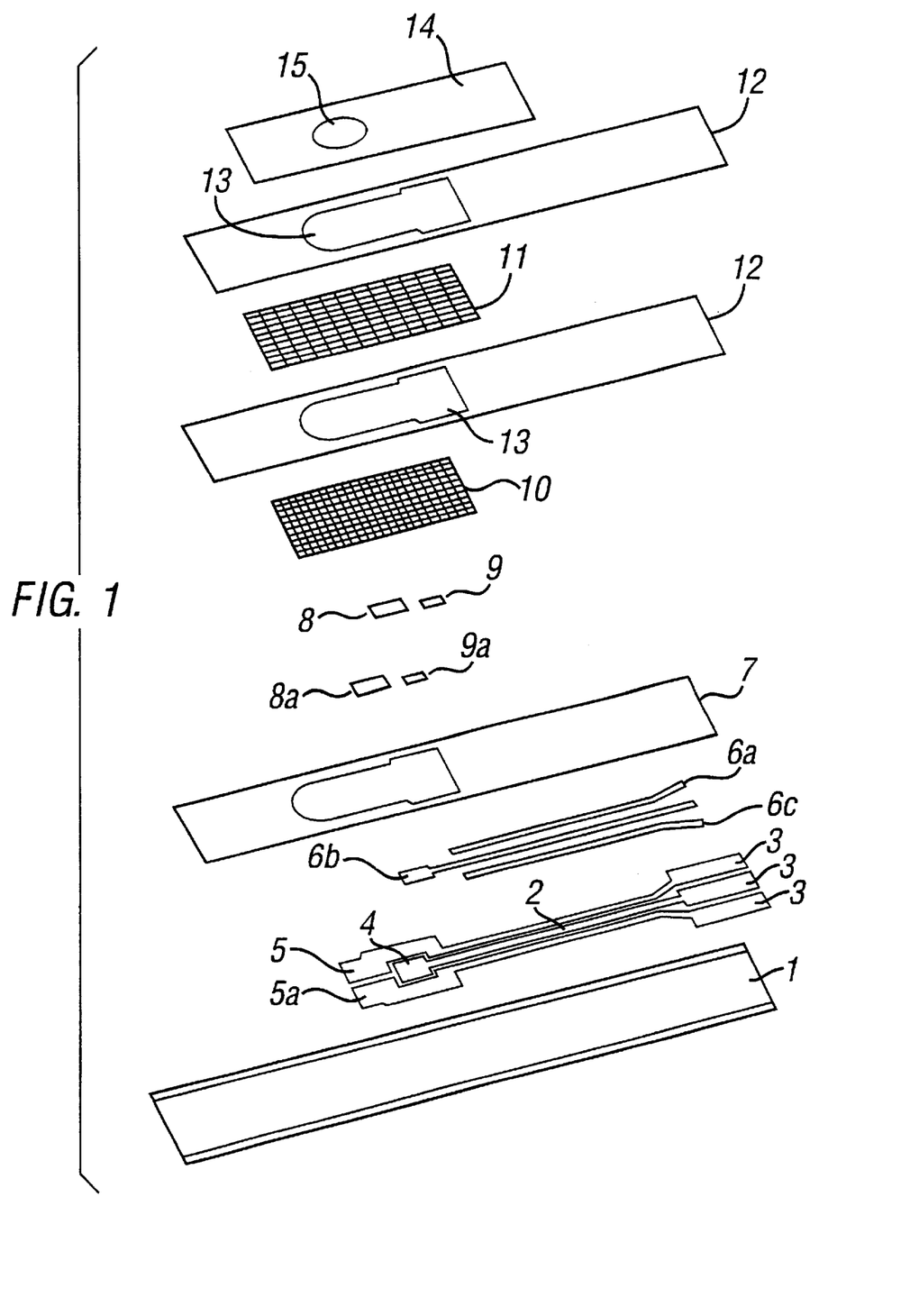
FIG. 1 is an exploded view of a biosensor strip according to one embodiment of this invention.
Figure 2:
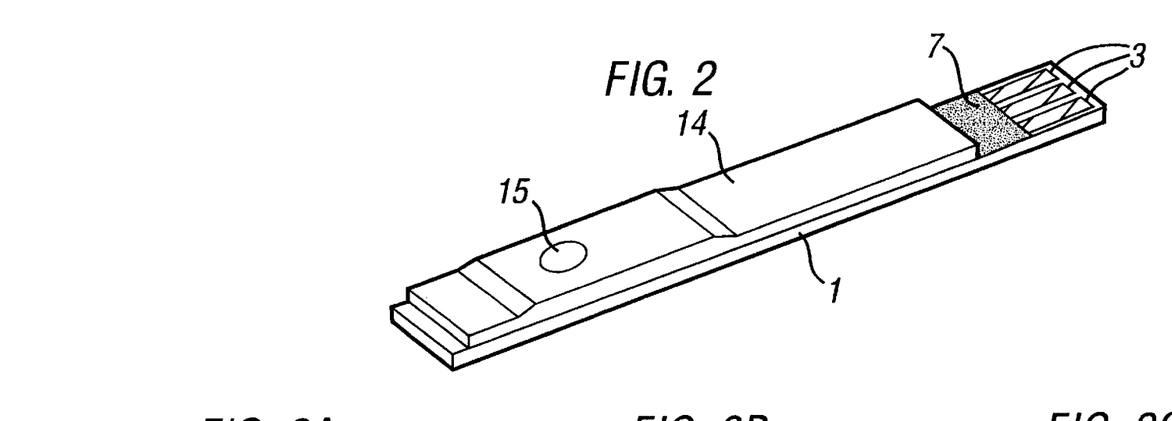
FIG. 2 is a perspective view of the assembled biosensor strip of FIG. 1.

A biosensor strip suitable for this invention is illustrated in FIGS. 1 and 2. Referring to FIGS. 1 and 2, an electrode support 1, preferably an elongated strip of polymeric material (e.g., polyvinyl chloride, polycarbonate, polyester, or the like) supports three tracks 2 of electrically conductive ink, preferably comprising carbon. These tracks 2 determine the positions of electrical contacts 3, a pseudo reference/counter electrode 4, a working electrode 5, and a dummy electrode 5a. The electrical contacts 3 are insertable into an appropriate measurement device (not shown). Although FIG. 1 illustrates a dummy electrode 5a, this dummy electrode 5a is optional and is not required for the operation of this invention.

Each of the elongated portions of the conductive tracks 2 can optionally be overlaid with a track 6a, 6b, and 6c of conductive material, preferably made of a mixture comprising silver particles and silver chloride particles. The enlarged exposed area of track 6b overlies pseudo reference/counter electrode 4. A layer of a hydrophobic electrically insulating material 7 further overlies the tracks 6a, 6b, and 6c. The positions of the pseudo reference/counter electrode 4, the working electrode 5, the dummy electrode 5a, and the electrical contacts 3 are not covered by the layer of hydrophobic electrically insulating material 7. This hydrophobic electrically insulating material 7 serves to prevent short circuits. Because this insulating material is hydrophobic, it can cause the sample to be restricted to the exposed electrodes. A preferred insulating material is commercially available as "POLYPLAST" (Sericol Ltd., Broadstairs, Kent, UK).

FIGS. 3A through 3E illustrate six different configurations of the electrode regions of the biosensor strips of this invention. Although FIGS. 3A through 3E illustrate a dummy electrode 5a, this dummy electrode 5a is optional and is not required for the operation of this invention. A control configuration of the electrode region of a biosensor strip is illustrated in FIG. 4. It can be seen that the control configuration lacks auxiliary areas, which will be described in detail below.

Electrode 5 is a layer of conductive material containing a working area 8 and an auxiliary area 9. The working area 8 is formed from a working ink, which is printed on the layer of conductive material of the electrode 5. The working ink comprises a mixture of a redox mediator, an enzyme, and a conductive material. Electrode 5a is a layer of conductive material containing a working area 8a and an auxiliary area 9a. The working area 8a is formed from a dummy ink, which is printed on the layer of conductive material of the electrode 5a. The dummy ink comprises a mixture of a redox mediator and a conductive material, but lacks an enzyme. Auxiliary areas 9 and 9a are printed on conductive layers of the electrodes 5 and 5a, respectively. Each of the auxiliary areas 9 and 9a is formed from a dummy ink that comprises a mixture of a redox species and a conductive material, but lacks an enzyme. The redox species included in the auxiliary area 9 is preferably the same as that included in the auxiliary area 9a. The redox species used in the dummy ink for the auxiliary areas can be the same as the redox mediator used in the dummy ink for the working area 8a. The redox mediator in the dummy ink for the working area 8a must be the same as the redox mediator included in the working area 8 that is deposited on the electrode 5 but need not be the same as the redox species used in the auxiliary areas 9 and 9a.

The auxiliary areas 9 and 9a are located closer to the pseudo reference/counter electrode 4 than is the working area 8a or the working area 8. The auxiliary areas 9 and 9a are positioned symmetrically with respect to the pseudo reference/counter electrode 4.

Referring to FIG. 4, the electrode 5a is a layer of conductive material containing a working area 8a. The electrode 5 is a layer of conductive material containing a working area 8. The working area 8 is formed from a working ink, which is printed on the layer of conductive material of the electrode 5. The working ink comprises a mixture of a redox mediator, an enzyme, and a conductive material. The working area 8a is formed from a dummy ink printed on the conductive layer of the electrode 5a. The dummy ink comprises a mixture of a redox mediator and a conductive material, but lacks an enzyme. The working area 8a is located adjacent to the pseudo reference/counter electrode 4 and the working electrode 5. The control biosensor strip shown in FIG. 4 does not include auxiliary areas 9 and 9a. The layers of conductive material of the electrodes 4, 5, and 5a can be printed with an ink containing carbon. An ink having a low carbon-content typically has a carbon content of from about 30 to about 31 weight percent and a resin content of from about 7 to about 9 weight percent. An ink having a high carbon-content ink typically has a carbon content of from about 42 to about 45 weight percent and a resin content of from about 7 to about 9 weight percent.

The physical sizes of the auxiliary areas for the configurations shown in FIGS. 3A through 3E and FIG. 4 are set forth in Table 1.

TABLE 1

Figure 3A:
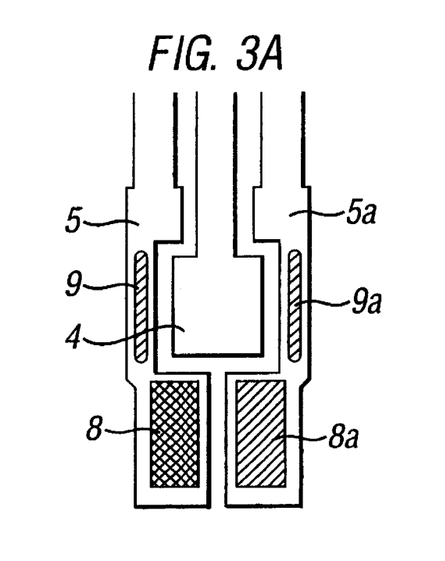
FIGS. 3A through 3E are schematic diagrams depicting the regions of a biosensor strip where the electrodes are disposed.
Figure 3B:
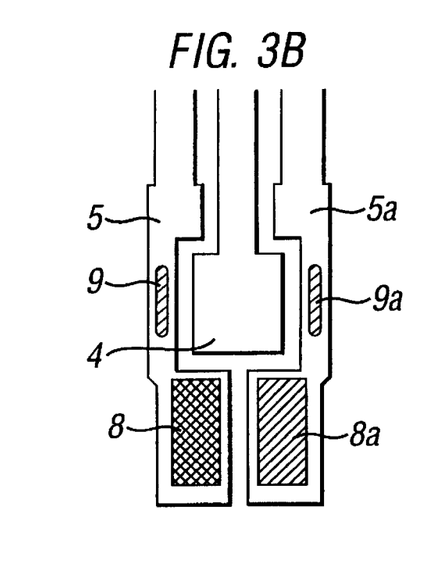
Figure 3C:
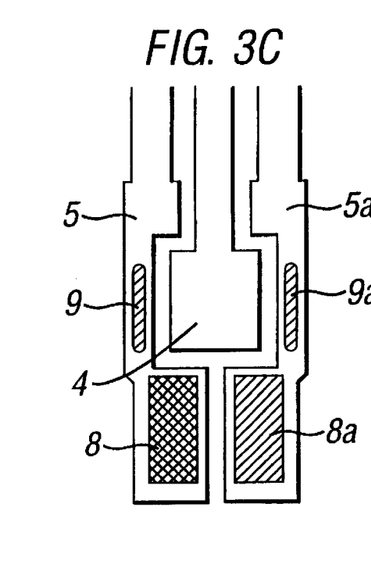
Figure 3D:
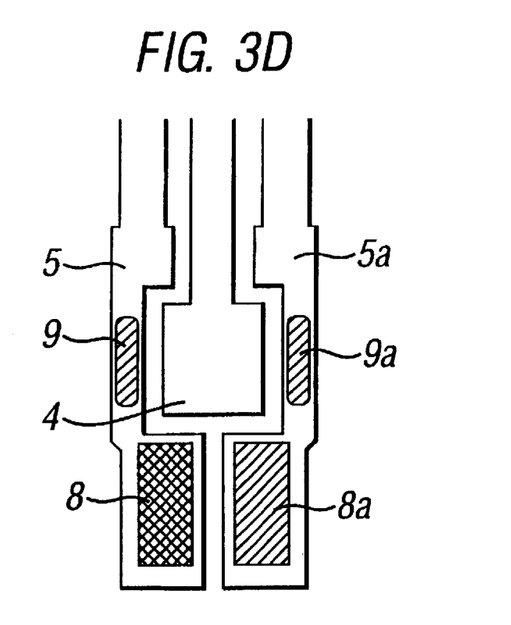
Figure 3E:
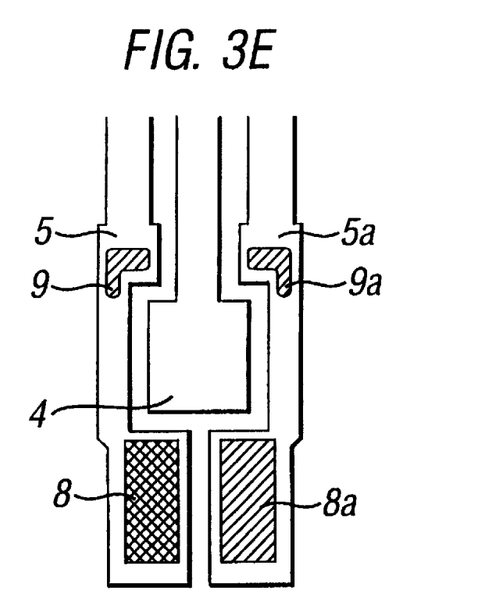
Figure 4:
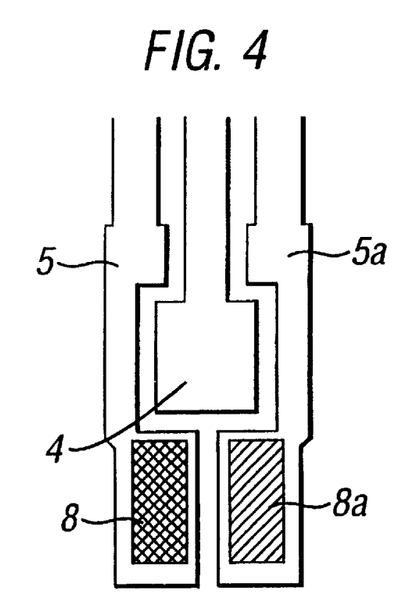
FIG. 4 is a schematic diagram depicting the regions of a control biosensor strip where the electrodes are disposed.

| Biosensor Strip Configuration | Auxiliary Area (mm$^2$) |
|---|---|
| Control (FIG. 4) | 0.000 |
| FIG. 3A | 0.398 |
| FIG. 3B | 0.230 |
| FIG. 3C | 0.296 |
| FIG. 3D | 0.609 |
| FIG. 3E | 0.366 |

The working area 8 is formed from a printing ink that includes a mixture of an enzyme, a redox mediator, and a conductive material. Alternatively, instead of an enzyme, working area 8 can contain a substrate that is catalytically reactive with an enzyme to be assayed. The working area 8a is formed from a printing ink that includes a mixture of a redox mediator and a conductive material without an enzyme. The auxiliary areas 9 and 9a are formed from printing inks that include a mixture of a redox species and a conductive material without an enzyme. The respective printing inks are applied to the electrodes 5 and 5a as discrete areas of fixed length. In a preferred embodiment, the conductive material comprises particles of carbon having the redox mediator adsorbed thereon.

A printing ink comprises an aqueous suspension of the conductive material having redox mediator adsorbed thereon. For the working electrode 5, the printing ink also includes an enzyme. For example, when the analyte to be measured is glucose in blood, the enzyme is preferably glucose oxidase, and the redox mediator is preferably ferrocene or a ferrocene derivative. In the alternative, for the working electrode 5, the printing ink can include a substrate in lieu of an enzyme when the analyte to be measured is an enzyme. The inks printed on the dummy electrode 5a lacks an enzyme or a substrate for an enzyme.

The printing inks can be screen-printed. The printing inks can further include a polysaccharide (e.g., a guar gum or an alginate), a hydrolyzed gelatin, an enzyme stabilizer (e.g., glutamate or trehalose), a film-forming polymer (e.g., a polyvinyl alcohol), a conductive filler (e.g., carbon), a defoaming agent, a buffer, or a combination of the foregoing.

The pseudo reference/counter electrode 4 is preferably situated relative to the working area 8 of the working electrode 5 and to the working area 8a of the dummy electrode 5a in such a manner that it is not in an ideal position for efficient electrochemical functioning. The electrodes 4, 5, and 5a are arranged so that the effect of the resistance of the sample on the overall resistance of the circuit is not minimized, as is conventional. Instead, the electrodes 4, 5, and 5a are arranged so that the resistance of the sample is maximized to the greatest extent possible while still being able to generate a response current capable of being detected by the measurement device used. To increase the resistance of the sample, the pseudo reference/counter electrode 4 is. preferably located as far as possible from the working electrode 5. When a dummy electrode 5a is used, the pseudo reference/counter electrode 4 is preferably located as far as possible from the working electrode 5a. A constraint that must be addressed is the maximum resistance of the sample that will allow a response current to be generated with the minimum acceptable volume of sample. The electrodes cannot be spaced so far apart that both the working electrode 5 and the pseudo reference/counter electrode 4 cannot be covered by the sample. When a dummy electrode 5a is employed, the electrodes 4 and 5a cannot be spaced so far apart that both the dummy electrode 5a and the pseudo reference/counter electrode 4 cannot be covered by the sample. It is preferred that the length of the path to be traversed by the sample (i.e., the sample path) be kept as short as possible in order to minimize the volume of sample required. The maximum length of the sample path can be as great as the length of the biosensor strip. However, the corresponding increase in resistance of the sample limits the length of the sample path to a distance that allows the necessary response current to be generated. The resistance of the sample is also influenced by the distance from the edge of the area of the pseudo reference/counter electrode 4 to the edge of the working area 8 of the working electrode 5. Reducing this distance by positioning the pseudo reference/counter electrode 4 downstream from the working electrode 5 increases the resistance of the sample. Positioning the electrodes contiguously is conventional. Positioning the electrodes in the manner of this invention has the further advantage of preventing completion of a circuit (and thus preventing detection of a response current) before the working electrode 5 has been completely covered by sample. When a dummy electrode 5a is used, the positioning of the dummy electrode 5a in relation to the pseudo reference/counter electrode 4 should be substantially similar to the positioning of the working electrode 5 relative to the pseudo reference/counter electrode 4, i.e., downstream.

A fine grade mesh layer 10 overlies the electrodes. This mesh layer 10 protects the printed components from physical damage. It also helps the sample to wet the pseudo reference/counter electrode 4 and the working electrode 5 (and the dummy electrode 5a, when used) by reducing the surface tension of the sample, thereby allowing it to spread evenly over the electrodes. Preferably, this mesh layer 10 extends over the entire length of the sample path, between and including the position at which the sample is introduced and the region where the electrodes are disposed. Preferably, this mesh layer 10 is constructed of finely woven nylon strands. Alternatively, any woven or non-woven material can be used, provided that it does not occlude the surface of the electrode such that normal diffusion of the sample is obstructed. The thickness of the mesh is selected so that the depth of the sample is sufficiently low that a high sample resistance is produced. Preferably, the mesh layer 10 is not more than 70 $\mu$m in thickness. Preferably the mesh layer 10 has a percent open area of about 40 to about 45%, a fiber count of about 95 to about 115 per cm, a fiber diameter of about 20 to about 40 $\mu$m, and a thickness of from about 40 to about 60 $\mu$m. A particularly preferred mesh is NY64 HC mesh, available from Sefar (formerly ZBF), CH-8803, Ruschlikon, Switzerland.

The mesh layer 10 can be coated with a surfactant. A surfactant coating is necessary only if the material of the mesh layer 10 itself is hydrophobic (for example, nylon or polyester). If a hydrophilic mesh layer is used, the surfactant coating can be omitted. The particular choice of surfactant is not critical, so long as it allows sufficiently uniform spreading of the sample. A preferred surfactant is "FC 170C FLUORAD" fluorochemical, surfactant (3M, St. Paul, Minn.). "FLUORAD" surfactant is a solution of a fluoroaliphatic oxyethylene adduct, lower polyethylene glycols, 1,4-dioxane, and water. A surfactant loading of from about 15 to about 20 $\mu$g/mg of mesh is preferred for most applications. The preferred surfactant loading will vary depending on the type of mesh layer and surfactant used and the sample to be analyzed. The preferred surfactant loading can be determined empirically by observing flow of the sample through the mesh layer 10 with different levels of surfactant.

A second layer of a coarser mesh 11 is preferably applied over the first layer of mesh. This second layer of mesh controls the rate of flow of the sample as it travels from the sample application point toward the reference and working electrode areas by providing spaces into which the displaced air within the sample path can move as the sample moves. The sample preferentially moves along the fine grade mesh layer 10 and partially in the coarse grade mesh layer 11. The spacing of the larger fibers of the second mesh layer 11, which are disposed perpendicular to the direction of flow of the sample, helps to control the rate of flow of the sample by presenting physical barriers to the movement of the sample as it travels along the sample path. The regular pattern of the fibers of the mesh ensures that the sample progresses in stages and that only samples having sufficient volume to generate an accurate response are able to pass all the way along the sample path and reach the pseudo reference/counter electrode 4.

Preferably, the mesh layer 11 is of a woven construction, so that it presents a regular repeating pattern of fibers disposed both perpendicular to and parallel to the longest aspect of the strip. Generally, the second layer of mesh should be substantially thicker than the first layer of mesh, with mesh fibers of larger diameter and larger spaces between them. The second layer of mesh preferably has a thickness of from about 100 to about 1000 $\mu$m, preferably from about 100 to about 150 $\mu$m. A mesh preferred for the second layer of mesh has an open area of about 50 to about 55%, a fiber count of from about 45 to about 55 per cm, and a fiber diameter of from about 55 to about 65 µm. A preferred mesh for the second layer of mesh is NY151 HC mesh, also available from Sefar, CH-8803, Rushchlikon, Switzerland. As is the case with the mesh layer 10, any woven or non-woven material can be used, provided that it does not occlude the surface of the electrode such that normal diffusion of the sample is obstructed.

The mesh layer 11 is also preferably provided with a coating of a surfactant (unless the mesh itself is hydrophilic), preferably the same surfactant as that used to coat the first layer of mesh. The loading of surfactant is lower on the layer of mesh 11 than on the layer of mesh 10, thereby providing a further barrier to movement of sample past the transverse fibers of the mesh 11. In general, a surfactant loading of from about 1 to about 10 µg/mg of mesh is preferred. The preferred surfactant loading can be determined empirically by observing flow of the sample through the mesh layer 11 with different levels of surfactant.

The mesh layers 10 and 11 are held in place by layers of hydrophobic electrically insulating ink 12. These layers of electrically insulating ink 12 are preferably applied by screen printing the ink over a portion of the peripheries of the mesh layers 10 and 11. Together, the layers of mesh and the layers of hydrophobic electrically insulating ink 12 surround and define a sample path 13 suitable for the sample to travel from the position at which the sample is introduced at one end of the strip towards the working electrode 5 (and the dummy electrode 5a, when used) and the pseudo reference/counter electrode 4. The hydrophobic electrically insulating ink 12 impregnates the layers of mesh outside of the sample path 13. The hydrophobic electrically insulating ink 12 thus defines the sample path 13 by preventing the sample from infiltrating the portions of the mesh layers covered by the layers of hydrophobic electrically insulating ink 12. A preferred hydrophobic electrically insulating ink 12 for impregnating the mesh layers is "SERICARD" (Sericol, Ltd., Broadstairs, Kent, UK).

The surfaces of the electrodes that are not in contact with the electrode support 1 are enclosed by a liquid impermeable cover membrane 14. This membrane 14 can be a flexible tape made of polyester or similar material. The membrane 14 includes a small aperture 15 to allow access of the applied sample to the underlying mesh layers 10 and 11. This liquid impermeable membrane 14 encloses the exposed surfaces of the working electrode 5 (and the dummy electrode 5a, when used) and the pseudo reference/counter electrode 4. Thus, the membrane 14 maintains the available sample space over the electrodes at a fixed depth, which is equivalent to the thickness of both mesh layers. The positioning of this membrane 14 ensures that the resistance of the sample is maintained at a high level. Any sample depth, up to the maximum depth of the two mesh layers, is adequate for this invention. The aperture 15 is positioned to overlie an end of the mesh area removed from the pseudo reference/counter electrode 4, such that the exposed mesh area beneath the aperture 15 can be used as a point of access or application for a liquid sample. Of course, the aperture 15 must overlie an end of the mesh area that is not covered by the hydrophobic electrically insulating ink 12. The size of this aperture 15 is not critical, but it should be sufficiently large to allow sufficient volume of sample to pass through to the mesh layers. The aperture 15 should not be so large as to allow any portion of the liquid sample to contact any of the electrodes before contacting a layer of mesh. The aperture 15 can be formed in the liquid impermeable cover membrane 14 by any suitable method (e.g., die punching). The liquid impermeable cover membrane 14 can be affixed to the biosensor strip by means of a suitable method of adhesion. Preferably, affixing is achieved by coating the underside of the flexible tape with a layer of hot melt glue, and then heat welding the tape to the surface of the layer of hydrophobic electrically insulating ink 12. The layer of hot melt glue typically has a coating weight of from about 10 to about 50 g/m$^2$, preferably from about 20 to about 30 g/m$^2$. Pressure sensitive adhesives or other equivalent methods of adhesion may also be used. Care should be taken when the tape is applied, because the heat and pressure applied to the tape layer can melt the "SERICARD" ink and can cause it to smear onto adjoining areas. Care should also be taken so that the tape does not cover the electrodes, the sample path 13, or the sample application area.

The upper surface of the liquid impermeable cover membrane 14 can also be provided with a layer of silicone or other hydrophobic material. This additional layer serves to drive the applied sample onto the portion of exposed mesh layers at the sample application point, thereby rendering the application of small volumes of sample much simpler.

In use, a biosensor strip of this invention is connected, via electrode contacts 3, to a measuring device (not shown). A liquid sample is applied through aperture 15, and the sample moves along the sample path 13. The progress of the sample is sufficiently impeded by the mesh layer 11, thereby allowing the sample to form a uniform flow front. Air is displaced through the upper portion of the mesh layer 11 to and through the aperture 15. The sample first completely covers the working electrode 5 (and the dummy electrode 5a, when used), and only then approaches and covers the pseudo reference/counter electrode 4, thereby completing the circuit and causing a response to be detected by the measuring device.

The following examples are intended to be illustrative and not limiting of the invention.

EXAMPLE 1

This example illustrates the effect of auxiliary areas on glucose response. Batches of biosensor strips having the configurations shown in FIGS. 3A through 3E were produced. A batch of control strips having the configuration shown in FIG. 4 was produced.

The batches were tested for non-monotonic current decay errors by means of an appropriate glucose meter with which the electrodes were compatible. The concentration of glucose was 30 mM. The results of the test are summarized in Table 2.

TABLE 2

| Type of biosensor strip | Percentage of error |
|---|---|
| Control (FIG. 4) | 97.8 |
| FIG. 3A | 2.2 |
| FIG. 3B | 0.0 |
| FIG. 3C | 0.0 |
| FIG. 3D | 7.8 |
| FIG. 3E | 11.1 |

Each of the biosensor strips that had auxiliary area (FIGS. 3A through 3E) had a lower percentage of error than did the Control (FIG. 4). Among the five different auxiliary area configurations tested, the smallest auxiliary area (FIG. 3B) had the lowest percentage of error. Rising transients can lead to erroneous readings.

EXAMPLE 2

Figure 5:
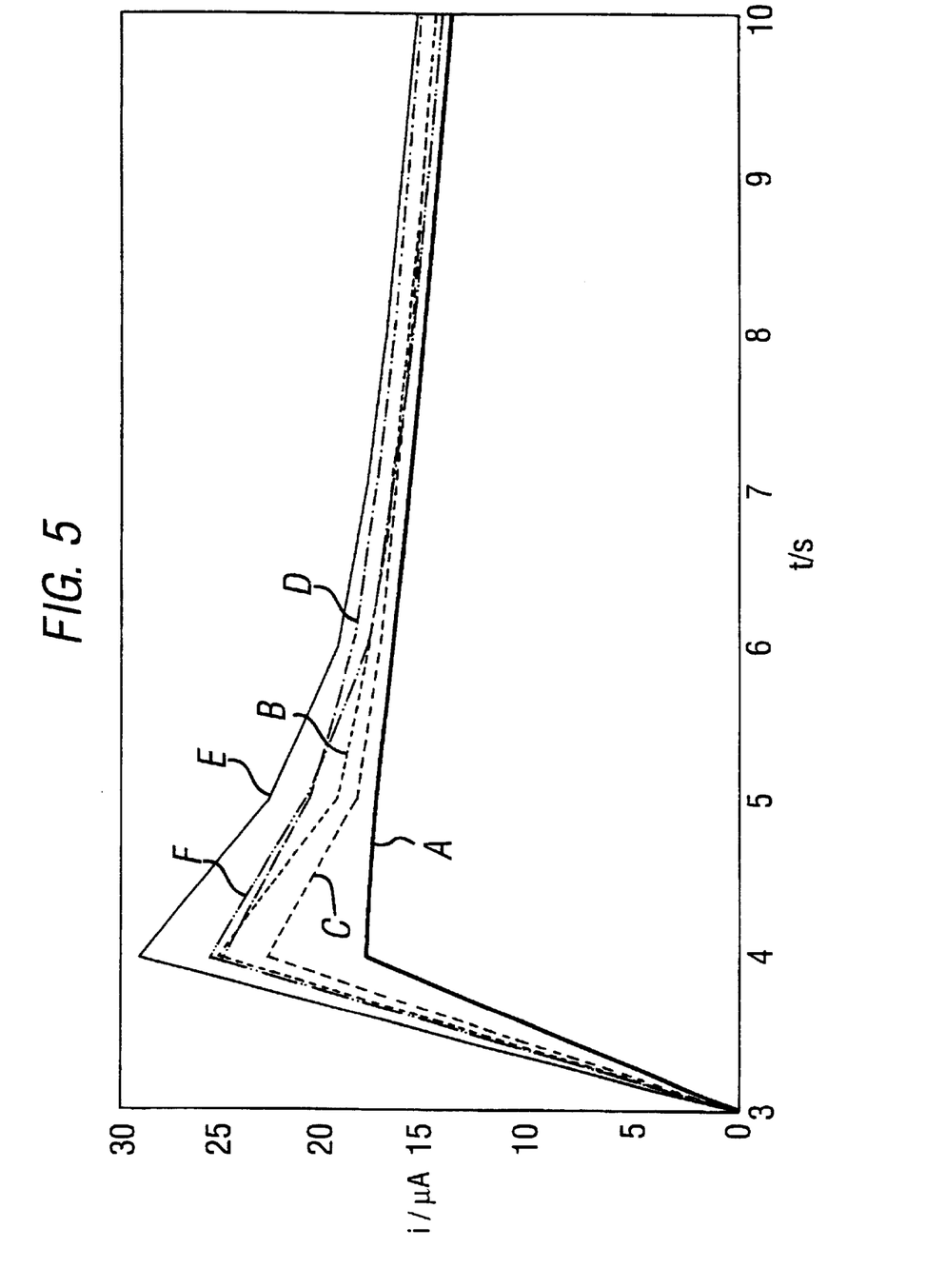
FIG. 5 is a graph depicting the current transients obtained from the working electrode when the biosensor strips of FIGS. 3A–3E and 2 were exposed to a sample containing 15 mM glucose.
Figure 6:
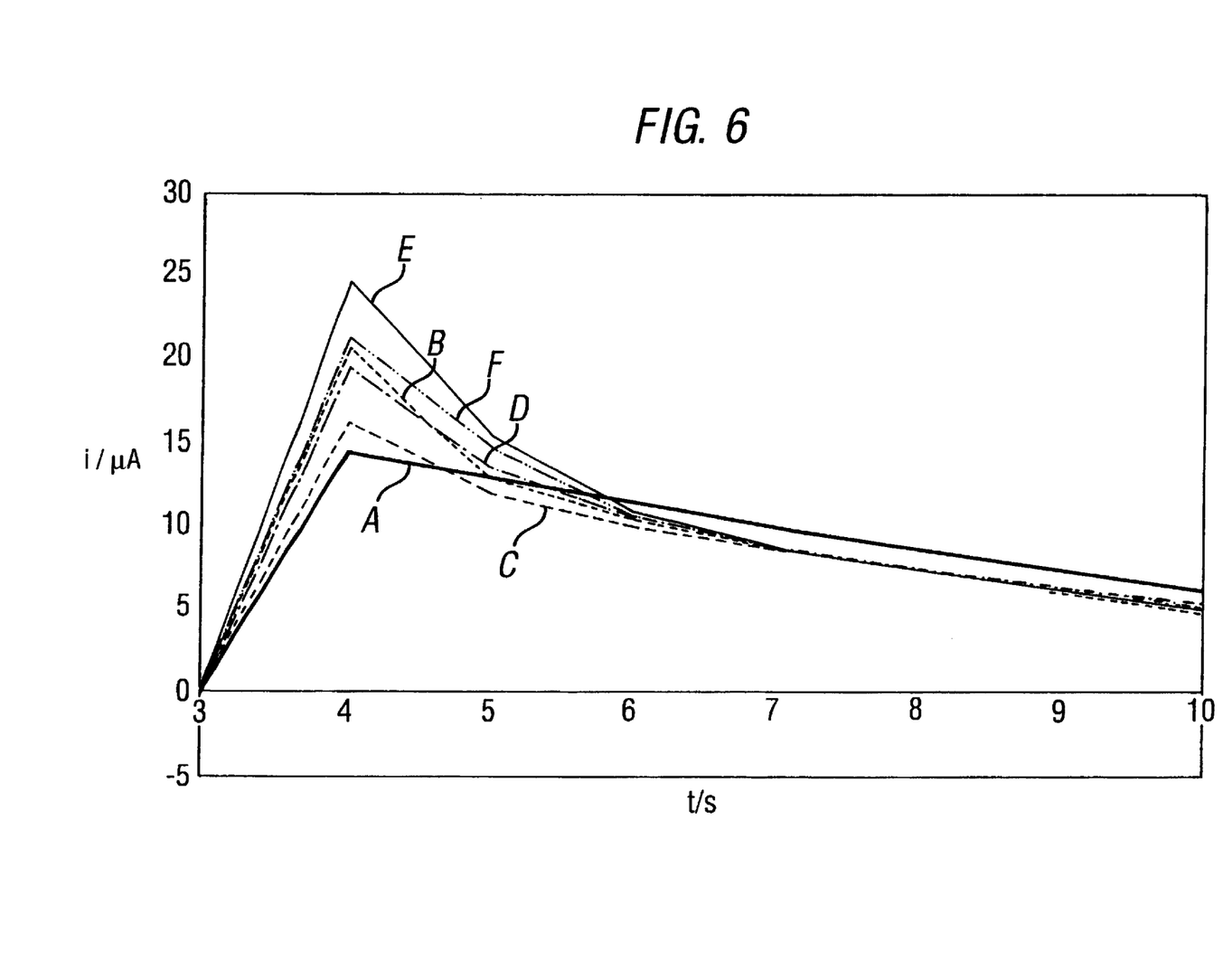
FIG. 6 is a graph depicting the current transients obtained from the dummy electrode when the biosensor strips of FIGS. 3A–3E and 2 were exposed to a sample containing 15 mM glucose.

This example illustrates the effect of auxiliary areas on current transients. Strips from the biosensor strip batches and strips from the control batch were contacted with blood samples containing about 15 mM glucose. Typical current-time decay transients were collected from the working electrode 5 and the dummy electrode 5a under the same test conditions as would be used by a glucose meter appropriate for these strips. The transients are shown in FIGS. 5 and 6. FIG. 5 is a graph illustrating the transients obtained from the working electrode 5. FIG. 6 is a graph illustrating the transients obtained from the dummy electrode 5a. In FIGS. 5 and 6, the curves for transients from the various electrode configurations are set forth in Table 3.

TABLE 3

| Curve | Electrode configuration |
|---|---|
| A | Control (FIG. 4) |
| B | FIG. 3A |
| C | FIG. 3B |
| D | FIG. 3C |
| E | FIG. 3D |
| F | FIG. 3E |

The curves in FIGS. 5 and 6 show that the configurations shown in FIGS. 3A through 3E had a larger current spike than did the control and an improved response current compared to that of the control, i.e., the response current was not non-monotonic.

EXAMPLE 3

This example illustrates the effect of auxiliary areas on the precision of measured glucose level. The effect of having an auxiliary area printed onto the normally exposed bare carbon surface of the working and dummy electrodes also helps to control the variable background current, which can arise from the oxidation/reduction at the carbon surface. The variable background current is caused by the ink printed in the auxiliary area. Also, the magnitude of the current generated from the oxidation of the redox species in the dummy ink is much larger than that from the variable background current. Control of the variable background current improves the precision of any reported glucose result obtained from these strips, because the current arising from the exposed carbon areas can vary from strip to strip, and the current can also vary between the signals from the working electrode 5 and the dummy electrode 5a from the same strip. The effect of the improvement of precision will vary depending on the quality and the pre-treatment of the carbon used to manufacture these strips; carbon of poor quality will experience the greatest improvement in precision, whereas carbon of good quality will experience less of an improvement. The results are shown in Table 4.

TABLE 4

| Biosensor strip type | Precision (% CV) |
|---|---|
| Control (FIG. 4) | 5.96 |
| FIG. 3A | 4.70 |
| FIG. 3B | 4.89 |
| FIG. 3C | 7.14 |
| FIG. 3O | 5.33 |
| FIG. 3E | 7.27 |

Other embodiments are within the scope of the claims. For example, the electrochemical cell can have a thin sample layer having a single mesh layer. The cell can employ small volumes of sample to measure analytes in the sample. Furthermore, in the case of analyzing blood samples, the hematocrit sensitivity of the cell is improved. The single layer of mesh can have a thickness of from about 100 μm to about 300 μm. Most preferably, the layer of mesh has a thickness of about 150 μm.

Furthermore, the sample-contacting areas of the working electrode 5 and the dummy electrode 5a can be equalized. The equalization of sample-contacting areas of the electrodes increases the accuracy and precision of the measurements of analyte concentration by balancing the background response from each electrode. The sample-contacting areas of the electrodes can be equalized by restricting the extent to which the overlying insulating layers encroach onto the conductive layers of the electrodes. The equalization of sample-contacting areas can be achieved by decreasing the width of the conductive layers of the electrodes and increasing the width of the electrode exposure region of the insulating layers in such a way that overlap of the insulating layer with the underlying conductive electrode layers is avoided or minimized. The configuration in which there is no overlap between the conductive layers and the insulating layers can increase the registration tolerance of the insulating layers, thereby minimizing this source of imprecision. The configuration can simplify the process of electrode production by permitting greater tolerance during registration of the different layers that contribute to the exposure of the conductive tracks.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An electrochemical cell comprising a first electrode, said first electrode comprising:
    a first working area, said first working area comprising a working ink; and
    a first auxiliary area, said first auxiliary area comprising a first dummy ink, wherein:
        said working ink comprises an enzyme and a first redox mediator; and
        said first dummy ink comprises a redox species but lacks an enzyme.
2. The electrochemical cell of claim 1, further comprising a pseudo reference/counter electrode.
3. The electrochemical cell of claim 1, wherein said first auxiliary area is located closer to said pseudo reference/counter electrode than is said first working area.
4. The electrochemical cell of claim 2, further comprising a second electrode, said second electrode comprising:
    a second working area, said second working area comprising a second dummy ink; and
    a second auxiliary area, said second auxiliary area comprising said first dummy ink,
    wherein said second dummy ink comprises said first redox mediator but lacks an enzyme.
5. The electrochemical cell of claim 4, wherein said second auxiliary area is located closer to said pseudo reference/counter electrode than is said second working area.
6. The electrochemical cell of claim 4, wherein said second working area is larger in area than is said second auxiliary area.
7. The electrochemical cell of claim 4, wherein said first working area is smaller in area than is the sum of the areas of said second working area and said second auxiliary area.
8. The electrochemical cell of claim 4, wherein said first redox mediator is a ferrocene or a ferrocene derivative and said redox species is a ferrocene or a ferrocene derivative.

9. The electrochemical cell of claim 4, wherein said enzyme is said working ink is glucose oxidase.

10. The electrochemical cell of claim 1, wherein said first working area is larger in area than said first auxiliary area.

11. A biosensor strip comprising:

an electrode support;

a first electrode disposed on said electrode support, said first electrode comprising:
  a first working area, said first working area comprising a working ink; and
  a first auxiliary area, said first auxiliary area comprising a first dummy ink, a second electrode disposed on said electrode support, said second electrode comprising:
  a second working area, said second working area comprising a second dummy ink; and
  a second auxiliary area, said second working area comprising said first dummy ink; and a pseudo reference/counter electrode disposed on said electrode support, said pseudo reference/counter electrode being spaced apart from said first electrode and said second electrode, wherein:
  said working ink comprises an enzyme and a first redox mediator;
  said first dummy ink lacks an enzyme and comprises a redox species; and
  said second dummy ink lacks an enzyme and comprises said first redox mediator.

12. The biosensor strip of claim 11, wherein said first auxiliary area is located closer to said pseudo reference/counter electrode than is said first working area.

13. The biosensor strip of claim 11, wherein said second auxiliary area is located closer to said pseudo reference/counter electrode than is said second working area.

14. The biosensor strip of claim 11, wherein said first working area is larger in area than said first auxiliary area.

15. The biosensor strip of claim 11, wherein said second working area is larger in area than said second auxiliary area.

16. The biosensor strip of claim 11, wherein said first working area is smaller in area than the sum of the areas of said second working area and said second auxiliary area.

17. The biosensor strip of claim 11, wherein said first redox mediator is a ferrocene or a ferrocene derivative and said redox species is a ferrocene or a ferrocene derivative.

18. The biosensor strip of claim 11, wherein said enzyme in said working ink is glucose oxidase.

19. The biosensor strip of claim 11, further comprising a covering layer defining an enclosed space over said electrodes, said covering layer having an aperture for receiving a sample into said enclosed space.

20. The biosensor strip of claim 19, further comprising a least one layer of mesh interposed in the enclosed space between said covering layer and said electrodes.

21. A method of manufacturing an electrochemical cell, said method comprising the steps of:
  applying a working ink to a first electrode to form a first working area; and
  applying a first dummy ink to said first electrode to form a first auxiliary area,
  wherein:
    said working ink comprises an enzyme and a first redox mediator; and
    said first dummy ink lacks an enzyme and comprises a redox species.

22. The method of claim 21, wherein said first working area is larger in area than said first auxiliary area.

23. The method of claim 21, further comprising the steps of:
  applying a second dummy ink to a second electrode to form a second working area; and
  applying said first dummy ink to said second electrode to form a second auxiliary area,
  wherein:
    said second dummy ink lacks an enzyme and comprises said first redox mediator.

24. The method of claim 23, wherein said second working area is larger in area than said first auxiliary area.

25. The method of claim 23, wherein said first redox mediator is a ferrocene or a ferrocene derivative and said redox species is a ferrocene or a ferrocene derivative.

26. The method of claim 23, wherein said enzyme in said working ink is glucose oxidase.

* * * * *